United States Patent
Imamura et al.

(10) Patent No.: US 7,087,326 B2
(45) Date of Patent: Aug. 8, 2006

(54) MOISTURE SENSOR AND FUEL CELL SYSTEM USING SAME

(75) Inventors: Tomonori Imamura, Kariya (JP); Toshiyuki Kawai, Toyohashi (JP)

(73) Assignee: Denso Corporation, Kariya (JP)

( * ) Notice: Subject to any disclaimer, the term of this patent is extended or adjusted under 35 U.S.C. 154(b) by 456 days.

(21) Appl. No.: 10/352,907

(22) Filed: Jan. 29, 2003

(65) Prior Publication Data

US 2003/0141188 A1    Jul. 31, 2003

(30) Foreign Application Priority Data

Jan. 31, 2002  (JP)  ............................. 2002-023868
Oct. 31, 2002  (JP)  ............................. 2002-318068

(51) Int. Cl.
*H01M 8/00*  (2006.01)
*H01M 8/04*  (2006.01)
*H01M 8/12*  (2006.01)

(52) U.S. Cl. .......................................... 429/12; 429/22
(58) Field of Classification Search ................. 429/12, 429/13, 34; 204/430
See application file for complete search history.

(56) References Cited

U.S. PATENT DOCUMENTS

| | | | |
|---|---|---|---|
| 5,393,404 A * | 2/1995 | Greenblatt et al. | ......... 204/430 |
| 6,337,009 B1 | 1/2002 | Nadanami et al. | |
| 6,696,186 B1 * | 2/2004 | Herdeg et al. | ................ 429/13 |

FOREIGN PATENT DOCUMENTS

| | | |
|---|---|---|
| JP | A 58-133773 | 8/1983 |
| JP | A 9-245826 | 9/1997 |
| JP | A 2000-243418 | 9/2000 |
| JP | A 2000-258390 | 9/2000 |
| JP | A 2001-236977 | 8/2001 |

* cited by examiner

*Primary Examiner*—Patrick Joseph Ryan
*Assistant Examiner*—Julian Mercado
(74) *Attorney, Agent, or Firm*—Oliff & Berridge, PLC

(57) ABSTRACT

A moisture sensor working to measure a moisture content of a specified measurement gas is provided which consists of an electrochemical cell having a first electrode exposed to the measurement gas and a second electrode exposed to a reference gas and a controller. The electrochemical cell outputs an electrical energy arising from chemical reaction of the measurement gas with the reference gas. The controller controls at least one of voltage appearing across and current flowing through the electrochemical cell and uses one of them to measure the moisture content of the measurement gas. This enables the moisture content to be determined free from the humidify of the measurement gas.

18 Claims, 12 Drawing Sheets

MOISTURE SENSOR AND FUEL CELL SYSTEM USING SAME

BACKGROUND OF THE INVENTION

1 Technical Field of the Invention

The present invention relates generally to an improved structure of a moisture sensor designed to measure a moisture content of a specified gas electrochemically and a fuel cell system using such a moisture sensor.

2 Background Art

Solid polymer fuel cells usually need to be humidified in order to keep the conductivity of an electrolyte film in the fuel cell. When a moisture content of the fuel cell is small, so that the electrolyte film is dry, it will cause an inner resistance of the fuel cell to be increased, thus resulting in a decrease in output voltage. Alternatively, when the moisture content of the fuel cell is too great, it will cause electrodes of the fuel cell to be covered with water, which disturbs diffusion of reactants: oxygen and hydrogen, resulting in a decrease in output voltage.

Thus, increasing the operating efficiency of the fuel cells requires fine control of a moisture content of the fuel cells precisely. For example, Japanese Patent First Publication No. 2001-236977 proposes a control system which measures the humidity of unreacted fuel cell exhaust gas using a humidity sensor and controls the amount of moisture added to the electrolyte film as a function of an output of the humidity sensor.

The humidity sensor, as employed in the above system, is of a capacitance type which is slow in response. Additionally, such a capacitance type humidity sensor encounters a difficulty in measuring the quantity of moisture correctly when the humidity is more than 100%, that is, when there are waterdrops.

SUMMARY OF THE INVENTION

It is therefore a principal object of the invention to avoid the disadvantages of the prior art.

It is another object of the invention to provide a moisture sensor designed to measure a moisture content of a gas precisely free from the humidity thereof.

It is a still object of the invention to provide a fuel cell system capable of monitoring and controlling the quantity of moisture contained in a fuel cell accurately.

According to one aspect of the invention, there is provided a moisture sensor which works to measure a moisture content of a specified measurement gas. The moisture sensor comprises: (a) an electrochemical cell having a first electrode exposed to the measurement gas and a second electrode exposed to a reference gas, the electrochemical cell outputting an electrical energy arising from chemical reaction of the measurement gas with the reference gas; (b) a voltage detector working to measure a voltage appearing at the electrochemical cell; (c) a current detector working to measure a current produced by the electrochemical cell; and (d) a controller controlling at least one of the voltage and the current of the electrochemical cell. One of the voltage and the current is used to determine the moisture content of the measurement gas. This structure enables the moisture content of the measurement gas to be determined free from the humidify of the measurement gas.

In the preferred mode of the invention, the measurement gas is one of a hydrogen gas or air. The reference gas is also one of a hydrogen gas or air.

The controller may determine the moisture content of the measurement gas as a function of a value of the current produced by the electrochemical cell when the voltage of the electrochemical cell is controlled to a given voltage value. The given voltage value may be altered depending upon the concentration of the gasses.

The controller may alternatively determine the moisture content of the measurement gas as a function of a value of the voltage of the electrochemical cell when the current produced by the electrochemical cell is controlled to a given current value. The given current value may be altered depending upon the concentration of the gasses.

According to the second aspect of the invention, there is provided a fuel cell system which comprises: (1) a moisture sensor working to measure a moisture content of a measurement gas, the moisture sensor including (a) an electrochemical cell having a first electrode exposed to the measurement gas and a second electrode exposed to a reference gas, the electrochemical cell outputting an electrical energy arising from chemical reaction of the measurement gas with the reference gas, (b) a voltage detector working to measure a voltage appearing at the electrochemical cell, (c) a current detector working to measure a current produced by the electrochemical cell, and (d) a controller controlling at least one of the voltage and the current of the electrochemical cell, the controller determining the moisture content of the measurement gas using one of the voltage and the current and providing a signal indicative thereof; (2) a fuel cell producing an electrical energy through chemical reaction between hydrogen and oxygen; (3) a moisture controlling mechanism working to control a quantity of moisture within the fuel cell; and (4) a system controller working to determine a moisture condition within the fuel cell using the signal outputted from the moisture sensor. The system controller actuates the moisture controlling mechanism to control the quantity of moisture within the fuel cell to a desired value based on the determined moisture condition.

In the preferred mode of the invention, if the measurement gas and the reference gas are identical in kind with each other, the controller works to bring a potential difference between the first and second electrodes of the moisture sensor to a given potential difference and determines that the quantity of moisture within the fuel cell is excessive when the current produced by the electrochemical cell is smaller than a first preselected current value.

Alternatively, if the measurement gas and the reference gas are different in kind from each other, the controller works to bring the voltage of the electrochemical cell to a given voltage and determines that the quantity of moisture within the fuel cell is excessive when the current produced by the electrochemical cell is smaller than a first preselected current value.

The controller determines that the fuel cell lacks in moisture content thereof when the current produced by the electrochemical cell is greater than a second preselected current value.

If the measurement gas and the reference gas are different in kind from each other, the controller may determine that the quantity of moisture within the fuel cell is excessive when a value of the voltage of the electrochemical cell under control in which the current flowing through the electrochemical cell is kept at a given current value is smaller than a first preselected voltage value.

If measurement gas and the reference gas are different in kind from each other, the controller may determine the fuel cell lacks in moisture content thereof when a value of the voltage of the electrochemical cell under control in which the current flowing through the electrochemical cell is kept at the given current value is greater than a second preselected voltage value.

If the measurement gas and the reference gas are identical in kind with each other, the controller may determine that the quantity of moisture within the fuel cell is excessive when the a potential difference between the first and second electrodes of the electrochemical cell under control in which the controller controls the current flowing through the electrochemical cell to a given current value is greater than a first preselected potential difference.

If the measurement gas and the reference gas are identical in kind with each other, the controller may determine that the fuel cell lacks in moisture content thereof when the potential difference between the first and second electrodes of the electrochemical cell under control in which the controller controls the current flowing through the electrochemical cell to the given current value is smaller than a second preselected potential difference.

The fuel cell system may further comprise an oxygen gas drain line through which an oxygen gas discharged from an oxygen electrode of the fuel cell flows and a hydrogen gas drain line through which a hydrogen gas discharged from a hydrogen electrode of the fuel cell flows. The moisture sensor may be installed in at least one of the oxygen gas drain line and the hydrogen gas drain line to measure a moisture content of at least one of the hydrogen gas and the oxygen gas discharged from the fuel cell.

The fuel cell system may further comprise an oxygen supply line through which an oxygen gas is supplied to the fuel cell and a hydrogen gas supply line through which a hydrogen gas is supplied to the fuel cell. The moisture sensor may alternatively be installed in at least one of the oxygen gas supply line and the hydrogen gas supply line to measure a moisture content of at least one of the hydrogen gas and the oxygen gas supplied to the fuel cell.

The moisture sensor may alternatively be installed within the fuel cell and work to measure a moisture content of at least one of an oxygen or a hydrogen gas within the fuel cell. In this case, the electrochemical cell of the moisture sensor is formed by a portion of the fuel cell.

According to the third aspect of the invention, there is provided a fuel cell system which comprises: (a) fuel cell stack including a plurality of cells each of which is made up of a pair of collection members and an electrolyte film disposed between the collection members; (b) a moisture sensor working to measure a quantity of moisture within at least one of the cells and output a signal indicative thereof; (c) a moisture controlling mechanism working to control a moisture content of the fuel cell stack; and (d) a system controller working to determine a moisture condition within the fuel cell stack using the signal outputted from the moisture sensor, the system controller actuating the moisture controlling mechanism to control the quantity of moisture within the fuel cell stack to a desired value based on the determined moisture condition. The moisture sensor includes (a) an electrochemical cell having electrodes formed by portions of the pair of collection members of the cell and the electrolyte film and (b) a resistance measuring circuit working to measure a resistance value of the electrochemical cell. The quantity of moisture within the cell is determined as a function of the resistance value of the electrochemical cell.

In the preferred mode of the invention, the resistance measuring circuit is designed to apply a sinusoidal wave signal to an output signal of the electrochemical cell and change a frequency of the sinusoidal wave signal to measure an AC impedance of the electrochemical cell. The resistance measuring circuit works to determine a resistance value of the electrolyte film and a reaction-caused resistance value of the electrodes of the electrochemical cell.

The system controller determines that the fuel cell stack lacks in moisture content thereof when the resistance value of the electrolyte film is greater than a first preselected resistance value.

The system controller determines that the quantity of moisture within the fuel cell stack lies within an allowable range when the resistance value of the electrolyte film is smaller than the first preselected resistance value and when the reaction-caused resistance value is smaller than a second preselected resistance value.

The system controller determines that the quantity of moisture within the fuel cell stack is excessive when the reaction-caused resistance value is greater than the second preselected resistance value.

The fuel cell system may further comprise moisture sensors installed in some of the cells of the fuel cell stack which are identical in structure with the moisture sensor.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Figure 1:
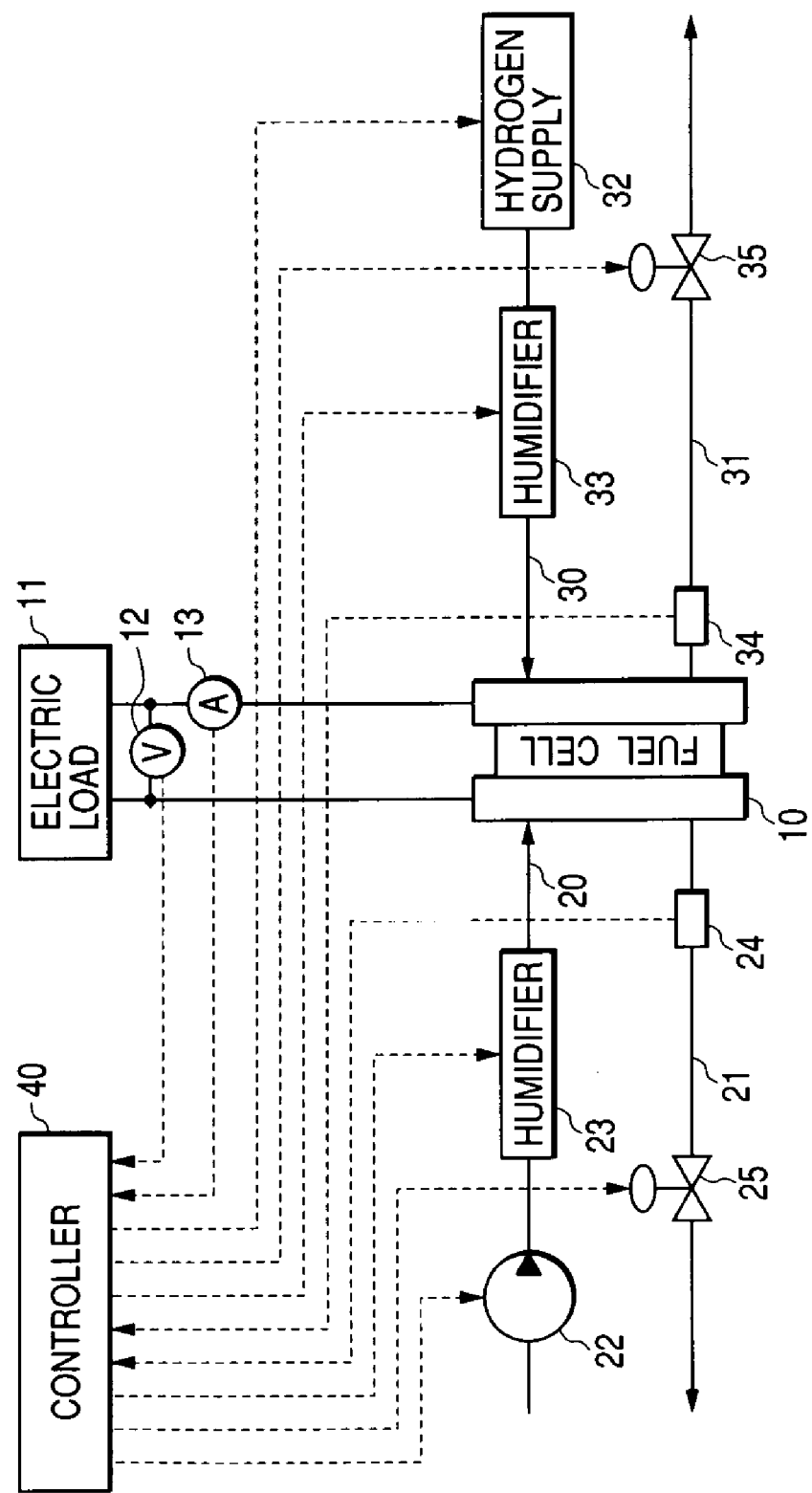
FIG. 1 is a block diagram which shows a fuel cell system according to the first embodiment of the invention.

Referring to the drawings, wherein like reference numbers refer to like parts in several views, particularly to FIG. 1, there is shown a fuel cell system according to the first embodiment of the invention which consists essentially of a fuel cell stack 10, an air supply device 22, a hydrogen supply device 32, humidifiers 23 and 33, moisture quantity sensors 24 and 34, and a controller 40.

The fuel cell stack 10 works to convert the energy produced by electrochemical reaction of oxygen and hydrogen into electric power. The fuel cell stack 10 is made up of a plurality of solid polyelectrolyte fuel cells. Each cell is made of a pair of electrodes (will also called an oxygen and a hydrogen electrode below) and an electrolyte film disposed between the electrodes. The fuel cell stack 10 is used to supply the power to an electric load 11. The fuel cell stack 10 is supplied with hydrogen and air (oxygen) and induces electrochemical reactions thereof at the electrodes which are of the forms:

Hydrogen electrode $H_2 \rightarrow 2H^+ + 2e^-$
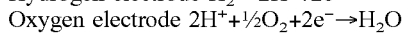
Oxygen electrode $2H^+ + \frac{1}{2}O_2 + 2e^- \rightarrow H_2O$ The above electrochemical reactions produce water. Additionally, humidified hydrogen and air gasses, as described later, supplied into the fuel cell stack 10 will cause condensate water to be produced therein. The moisture is, thus, produced both in a hydrogen flow path and in an air flow path within the fuel cell stack 10.

The fuel cell system also includes a voltage sensor 12 and a current sensor 13. The voltage sensor 12 works to measure an output voltage of the fuel cell stack 10 and outputs a signal indicative thereof to the controller 40. The current sensor 13 works to measure an output current of the fuel cell stack 10 and outputs a signal indicative thereof to the controller 40.

The fuel cell system also has an oxygen supply line 20 for supplying oxygen-contained air to oxygen electrodes (i.e., positive electrodes) of the fuel cell stack 10, an oxygen drain line 21 for draining an oxygen exhaust gas containing oxygen not consumed in the electrochemical reactions from the fuel cell stack 10, a hydrogen supply line 30 for supplying hydrogen gas to hydrogen electrodes (i.e., negative electrodes) of the fuel cell stack 10, and a hydrogen drain line 31 for draining a hydrogen exhaust gas containing hydrogen not consumed in the electrochemical reactions.

The air supply device 22 is located on the most upstream of the oxygen supply line 20 and may be implemented by a compressor. The hydrogen supply device 32 is located on the most upstream of the hydrogen supply line 30 and may be implemented by a reformer working to produce hydrogen through reforming reactions or a hydrogen tank having disposed therein a hydrogen storage such as a hydrogen absorbing alloy in which pure hydrogen is stored. The air supply device 22 and the hydrogen supply device 32 have regulators capable of regulating a supplied amount of air (i.e., oxygen) and hydrogen, respectively.

The electrochemical reactions within the fuel cell stack 10 require the electrolyte films of the cells to be moist. This condition is established by the humidifiers 23 and 33 disposed in the oxygen supply line 20 and the hydrogen supply line 30 which work to humidify the air and hydrogen supplied to the fuel cell stack 10. The humidifiers 23 and 33 have regulators capable of regulating the amount of moisture to be added to the air and hydrogen, respectively.

The moisture quantity sensors 24 and 34 are disposed in the oxygen drain line 21 and the hydrogen drain line 31 which work to measure the quantity of moisture contained in the oxygen exhaust gas and the hydrogen exhaust gas, respectively.

The fuel cell system also includes an air back-pressure regulator valve 25 and a hydrogen back-pressure regulator valve 35 disposed in the oxygen drain line 21 and the hydrogen drain line 31, respectively. The air back-pressure regulator valve 25 works to regulate the pressure of air flowing through the oxygen supply line 20 and the fuel cell stack 10. The regulation of the air pressure within the oxygen supply line 20 and the fuel cell stack 10 is achieved by controlling the degree of opening of the valve 25 since the air to be supplied to the fuel cell stack 10 is pressurized by the compressor 22. Similarly, the hydrogen back-pressure regulator valve 35 works to regulate the pressure of hydrogen gas flowing through the hydrogen supply line 30 and the fuel cell stack 10.

When each of the back-pressure regulator valves 25 and 35 is moved toward a valve-open position, it will result in an increase in gas flow velocity, which causes the quantity of moisture staying within the fuel cell stack 10 to decrease. Conversely, when the back-pressure regulator valves 25 and 35 are shifted toward a valve-closed position, it will result in a rise in pressure of the hydrogen gas and increase in flow velocity thereof, which causes the quantity of moisture staying within the fuel cell stack 10 to increase. The adjustment of the gas flow velocity (i.e., the amount of moisture staying within the fuel cell stack 10) may also be achieved by regulating the amount of air supplied from the air supply device 22 or the amount of hydrogen gas supplied from the hydrogen supply device 32.

Specifically, the quantity of moisture within the fuel cell stack 10 may be controlled using one of the humidifiers 23 and 33, the back-pressure regulator valves 25 and 35, the air supply device 22, and the hydrogen supply device 32 or a combination of some or all of them.

The controller 40 receives outputs of the voltage sensor 12, the current sensor 13, and the moisture quantity sensors 24 and 34 and works to output control signals to the air supply device 22, the hydrogen supply device 32, the humidifiers 23 and 33, and the back-pressure regulator valves 25 and 35.

Figure 2:
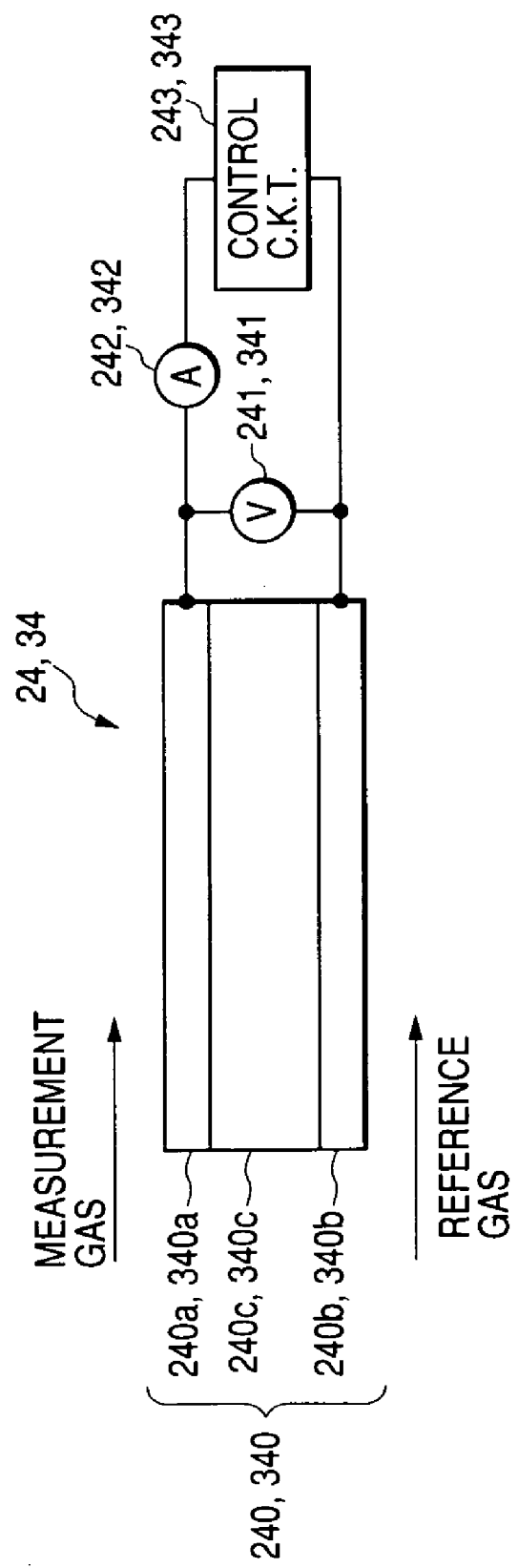
FIG. 2 is a circuit diagram which shows a moisture quantity sensor employed in the fuel cell system of FIG. 1.

The moisture quantity sensor 24, as clearly shown in FIG. 2, consists of an electrochemical cell 240 made up of a measurement gas electrode 240a, a reference gas electrode 240b, and a solid electrolyte 240c retained between the electrodes 240a and 240b, a voltage detector 241, a current detector 242, and a control circuit 243. The electrodes 240a and 240b each support catalyst. The voltage detector 241 works to measure the voltage between the electrodes 240a and 240b. The current detector 242 works to measure the current flowing through the electrochemical cell 240. The control circuit 243 works to control the voltage and current of the electrochemical cell 240.

Similarly, the moisture quantity sensor 34 consists of an electrochemical cell 340 made up of a measurement gas electrode 340a, a reference gas electrode 340b, and a solid electrolyte 340c retained between the electrodes 340a and 340b, a voltage detector 341, a current detector 342, and a control circuit 343. The electrodes 340a and 340b each carry catalyst. The voltage detector 341 works to measure the voltage developed between the electrodes 340a and 340b. The current detector 342 works to measure the current flowing through the electrochemical cell 340. The control circuit 343 works to control the voltage and current of the electrochemical cell 340.

The measurement gas electrodes 240a and 340a of the moisture quantity sensors 24 and 34 are respectively exposed to the air and hydrogen gases emitted from the fuel cell stack 10 which are to be measured in moisture content. The reference gas electrodes 240b and 340b need to be constant in electric potential and are exposed to air or hydrogen gas used as a reference gas whose moisture content is known. In this embodiment, the measurement gasses to which the measurement gas electrodes 240a and 340a are exposed are different from the reference gasses to which the reference gas electrodes 240b and 340b are exposed. Specifically, if the air is used as the measurement gas, the hydrogen gas is used as the reference gas.

When the electrochemical cell 240 is exposed at the measurement gas electrode 240a and the reference gas electrode 240b to the air and hydrogen gasses, respectively, it will generate electric potential between the electrodes 240a and 240b. If the air is used as the reference gas, it may be provided from the atmosphere. Alternatively, if the hydrogen gas is used as the reference gas, it may be provided from the hydrogen supply device 32. The same applies to the electrochemical cell 340.

Figure 3:
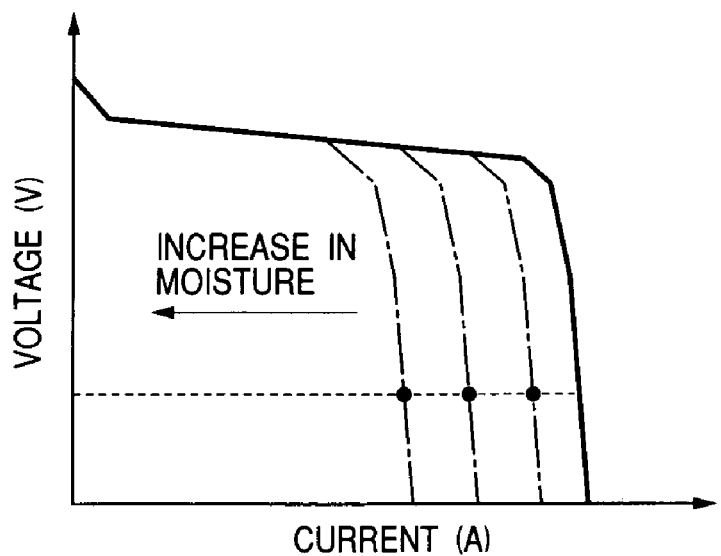
FIG. 3 is a graph which shows sensor characteristics of the moisture quantity sensor of FIG. 2.

FIG. 3 shows sensor characteristics of the moisture quantity sensors 24 and 34. A solid line indicates a voltage-current relation in a case where the measurement gas contains a desired quantity of moisture. As the moisture content of the measurement gas increases, a relative concentration of oxygen or hydrogen contained in the measurement gas decreases, thus resulting in a decrease in limiting current, as illustrated by broken lines, to be outputted by the electrochemical cells 240 and 340. Specifically, decreasing of the value of current produced by the electrochemical cells 240 and 340 as a function of an increase in moisture content of the measurement gas is established by controlling the voltage developed by the electrochemical cells 240 and 340 to a constant level.

Figure 4:
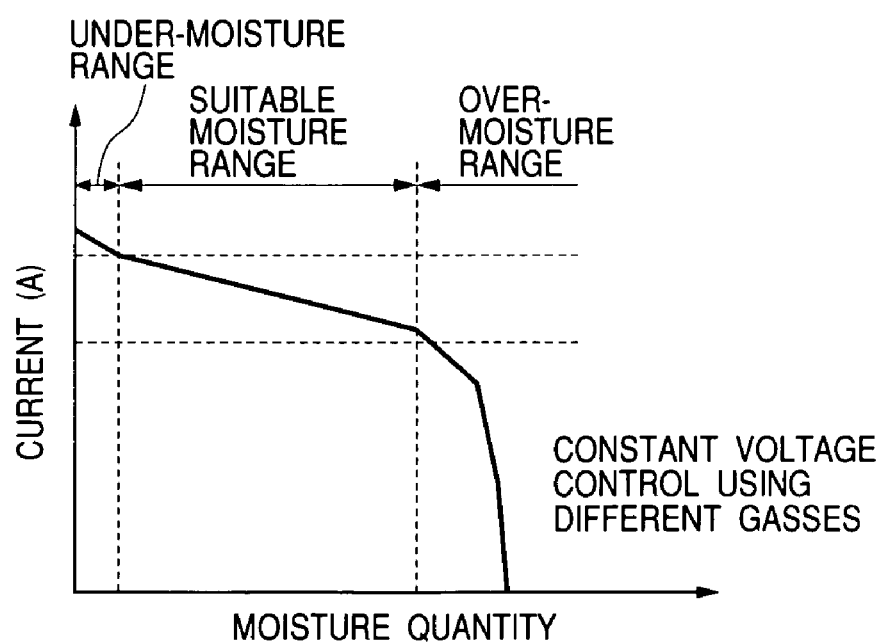
FIG. 4 is a graph which shows a relation between the quantity of moisture contained in a measurement gas and an output current of an electrochemical cell when the moisture quantity sensor is controlled to a constant voltage in a case where the measurement gas and reference gas are different in kind from each other.

FIG. 4 is a graph which shows a relation between the quantity of moisture contained in the measurement gas and an output current of the electrochemical cells 240 and 340 when the moisture quantity sensors 24 and 34 are controlled in voltage to a constant level in a case where the measurement gas and reference gas are different in kind from each other. The graph shows that the measurement gas and the output current have a correlation which will be discussed below in detail.

Keeping a potential difference between the electrodes of each of the sensors 24 and 34 constant under the constant voltage control, as described above, requires keeping a difference in gas concentration between the electrodes constant. When the moisture content of the measurement gas is increased, it will cause the concentration of oxygen or hydrogen to be decreased, thus resulting in a decrease in quantity of oxygen or hydrogen of the measurement gas consumed in adjusting the concentration of oxygen or hydrogen on the electrode to a desired value. Specifically, an increase in quantity of moisture contained in the measurement gas results in a decrease in quantity of oxygen or hydrogen of the measurement gas, thus resulting in a decrease in output current of the sensors 24 and 34.

Accordingly, a determination of the quantity of moisture within the fuel cell stack 10 may be made by placing the sensors 24 and 34 under the constant voltage control and measuring a resulting value of current produced therefrom. In practice, when the current outputted from the sensors 24 and 34 decreases below a first preselected value, the controller 40 determines that the quantity of moisture in the fuel cell stack 10 has increased over an allowable or suitable range. When the current output exceeds a second preselected value higher in level than the first preselected value, the controller 40 determines that the fuel cell stack 10 lacks in moisture content.

Figure 5:
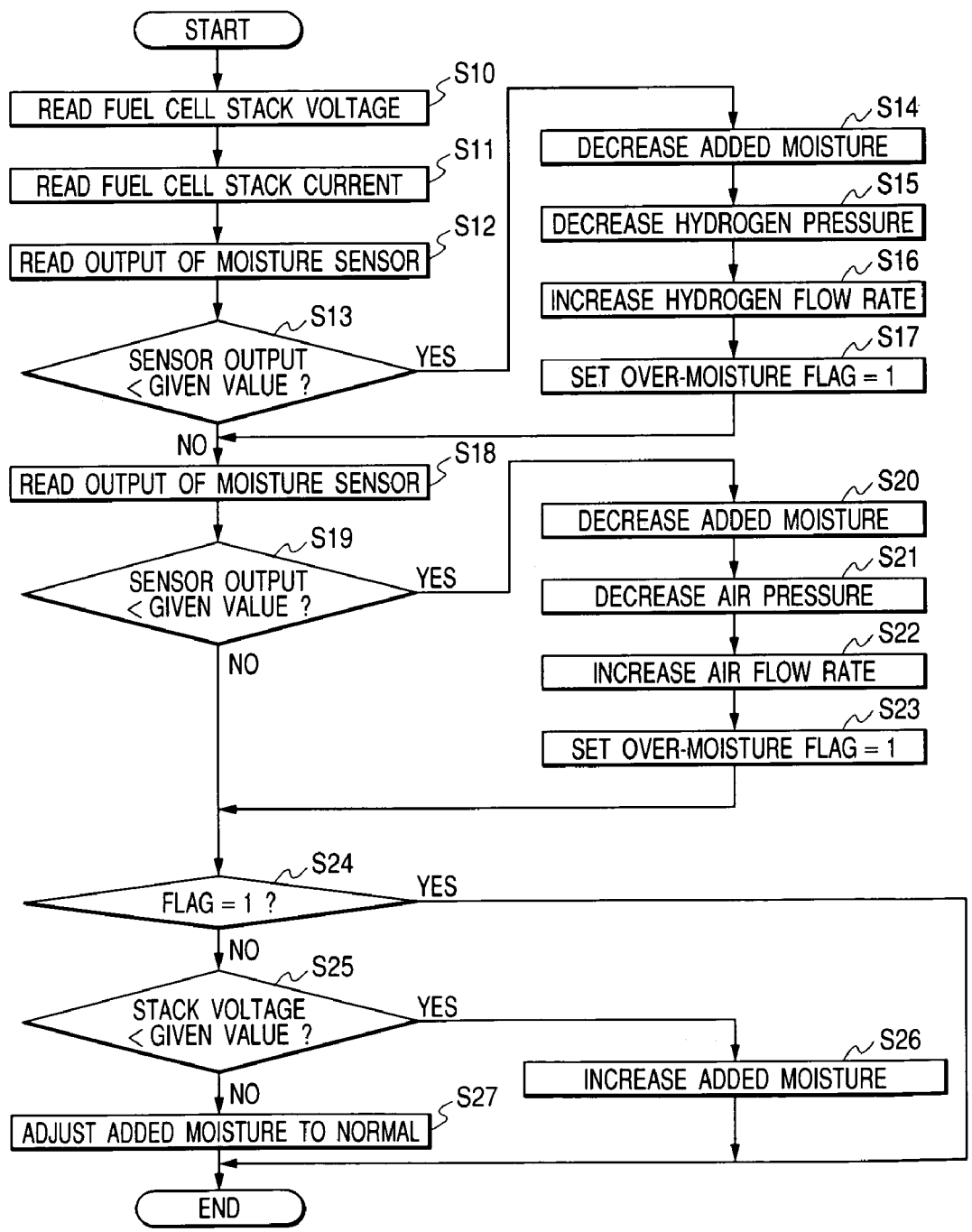
FIG. 5 is a flowchart of a moisture control program executed by the fuel cell system of FIG. 1.

FIG. 5 is a flowchart of a program or sequence of logical steps executed in the controller 40.

After entering the program, the routine proceeds to step 10 wherein the value of voltage output of the fuel cell stack 10 is measured using an output of the voltage sensor 12. The routine proceeds to step 11 wherein the value of current output of the fuel cell stack 10 is measured using an output of the current sensor 13.

The routine proceeds to step 12 wherein an output (i.e., a current value) of the moisture quantity sensor 34 installed in the hydrogen drain line 31 is monitored. The routine proceeds to step 13 wherein it is determined whether the output of the moisture quantity sensor 34 is smaller than a preselected value or not. It a YES answer is obtained meaning that the quantity of moisture on the side of the hydrogen electrodes of the fuel cell stack 10 is excessive, then the routine proceeds to a sequence of steps 14 to 17 to decrease a moisture content of the fuel cell stack 10.

Specifically, in step 14, the humidifier 33 is controlled to decrease the amount of moisture added to the hydrogen gas supplied to the fuel cell stack 10 through the hydrogen supply line 30. The routine proceeds to step 15 wherein the hydrogen back-pressure regulator valve 35 is opened further to decrease the hydrogen pressure, thereby increasing the flow velocity inside the fuel cell stack 10. The routine proceeds to step 16 wherein the hydrogen supply device 32 is controlled to increase the flow velocity of the hydrogen gas supplied therefrom. The routine proceeds to step 17 wherein an over-moisture flag is raised.

If a NO answer is obtained in step 13 or after step 17, the routine proceeds to step 18 wherein an output (i.e., a current value) of the moisture quantity sensor 24 installed in the oxygen drain line 21 is monitored. The routine proceeds to step 19 wherein it is determined whether the output of the moisture quantity sensor 24 is smaller than a preselected value or not. It a YES answer is obtained meaning that the quantity of moisture on the side of the oxygen electrodes of the fuel cell stack 10 is excessive, then the routine proceeds to a sequence of steps 20 to 23 to decrease a moisture content of the fuel cell stack 10.

Specifically, in step 20, the humidifier 23 is controlled to decrease the amount of moisture added to the air supplied to the fuel cell stack 10 through the oxygen supply line 20. The routine proceeds to step 21 wherein the oxygen back-pressure regulator valve 25 is opened further to decrease the air pressure, thereby increasing the flow velocity of the oxygen gas in the fuel cell stack 10. The routine proceeds to step 22 wherein the air supply device 22 is controlled to increase the flow velocity of the air supplied therefrom. The routine proceeds to step 23 wherein the over-moisture flag is raised.

If a NO answer is obtained in step 19 or after 23, the routine proceeds to step 24 wherein it is determined whether the over-moisture flag is raised or not. If a YES answer is obtained, then the routine terminates the moisture control. Alternatively, if a NO answer is obtained meaning that the over-moisture flag is not raised, then the routine proceeds to step 25 wherein a voltage output of the fuel cell stack 10 is lower than a preselected value or not. Specifically, the controller 40 stores therein a map indicating a relation between the output current and the output voltage of the fuel cell stack 10 and determines whether the voltage output, as measured in step 10, is lower than a voltage value which corresponds in the map to the current output, as measured in step 11, or not.

If a YES answer is obtained meaning that a moisture content of the fuel cell stack 10 is not excessive and that the output of the fuel cell stack 10 is dropping, it may be concluded that the fuel cell stack 10 lacks in moisture content. The routine proceeds to step 26 wherein the humidifiers 23 and 33 are controlled to increase the quantity of moisture added to the air and the hydrogen gas, thereby increasing the moisture content of the fuel cell stack 10. Additionally, the back-pressure regulator valves 25 and 35 may also be brought to a closed position to decrease the flow velocity of the gasses outputted from the air supply device 22 and the hydrogen supply device 32.

Alternatively, if a NO answer is obtained in step 25 meaning that the moisture content of the fuel cell stack 10 is adequate to operate the fuel cell stack 10 normally, then the routine proceeds to step 27 wherein the quantity of moisture outputted from the humidifiers 23 and 33 is adjusted to a normal quantity to keep the moisture content of the fuel cell stack 10 as it is.

As apparent from the above discussion, the fuel cell system of this embodiment is designed to measure a moisture content of exhaust gasses from the fuel cell stack 10 using the moisture quantity sensors 24 and 34 made of the electrochemical cells 240 and 340 to determine a moisture condition within the fuel cell stack 10. The use of the electrochemical cells 240 and 340 enables the moisture content of the measurement gasses to be determined regardless of the temperature thereof and also results in an improved response rate of the sensors 24 and 34 as compared with capacitance type humidity sensors.

The fuel cell system of the second embodiment will be described below with reference to FIG. 6 which is different from the first embodiment in that the current flowing through each of the moisture quantity sensors 24 and 34 is controlled at a constant level.

Figure 6:
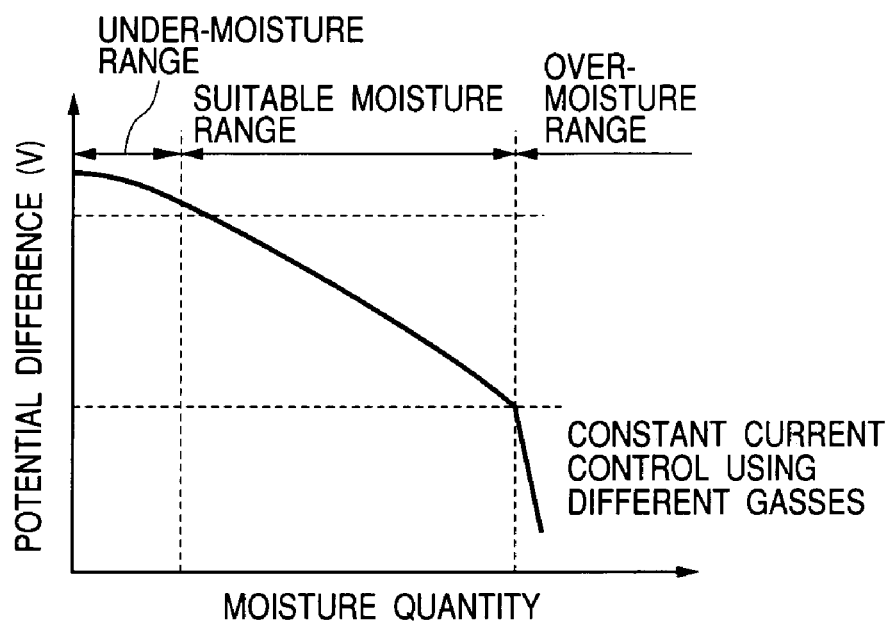
FIG. 6 is a graph which illustrates a relation between a moisture content of a measurement gas and a potential difference between electrodes of a moisture quantity sensor when it is placed under constant current control in a case where the measurement gas and reference gas are different in kind from each other.

FIG. 6 illustrates a relation between a moisture content of the measurement gas and a potential difference between the electrodes of the moisture quantity sensors 23 and 34 when they are placed under the constant current control in a case where the measurement gas and the reference gas are different in kind from each other. The moisture content of the measurement gas and the potential difference have a correlation as discussed below.

Usually, the quantity of hydrogen or oxygen gas consumed on the electrodes of the moisture quantity sensors 24 and 34 is constant when the current flowing through the moisture quantity sensors 24 and 34 is controlled at a constant level, but however, the concentration of hydrogen or oxygen on the measurement gas electrodes 240a and 340a decreases with an increase in moisture content of the measurement gas, thereby resulting in a change in potential difference between the measurement and reference gas electrodes. Specifically, when the moisture content of the measurement gas increases, it will result in a relative decrease in hydrogen or oxygen concentration of the measurement gas, which causes the potential difference between the measurement and reference gas electrodes to be decreased. Therefore, a determination of the quantity of moisture within the fuel cell stack 10 may be made by placing the electrochemical cells 240 and 340 of the moisture quantity sensors 24 and 34 under the constant current control and measuring the potential difference between the measurement and reference gas electrodes. In practice, when the potential difference decreases below a first preselected value, the controller 40 determines that the quantity of moisture in the fuel cell stack 10 has increased over a suitable range. When the potential difference exceeds a second preselected value higher in level than the first preselected value, the controller 40 determines that the fuel cell stack 10 lacks in moisture content. Other arrangements and operations of the fuel cell system are identical with those in the first embodiment, and explanation thereof in detail will be omitted here.

The fuel cell system of the third embodiment will be described below with reference to FIGS. 7 and 8 which is different from the first embodiment in a combination of the measurement and reference gasses. Other arrangements are identical, and explanation thereof in detail will be omitted here.

The measurement gas and the reference gas used in each of the moisture quantity sensors 24 and 34 are identical in kind with each other. Specifically, when the measurement gas is hydrogen gas, hydrogen gas is also used as the reference gas. Alternatively, when the measurement gas is air, air is also used as the reference gas. The control circuits 243 and 343 of the moisture quantity sensors 24 and 34 in this embodiment also work as a voltage applying circuit.

In a case where the measurement gas and the reference gas are identical in kind, a difference in concentration between the measurement and reference gasses arising from a difference in moisture content thereof will result in a change in output of each of the moisture quantity sensors 24 and 34 produced by passage of hydrogen or oxygen ions through a corresponding one of the electrolytes 240c and 340c. Sensor characteristics of the moisture quantity sensors 24 and 34 when the measurement and reference gases are identical in kind are the same as those of FIG. 3 as discussed in the first embodiment.

In a case where air is used as the reference gas, the supply of the reference gas may be achieved, like the first embodiment, with the ambient air. In a case of hydrogen gas, the supply of the reference gas may be achieved using the hydrogen supply device 32. Moreover, in a case where the measurement and reference gasses are made of hydrogen gas, hydrogen gas containing moisture may be supplied to the measurement gas electrode 340a so that hydrogen ions having passed through the electrolyte 340c may be pumped out by the reference gas electrode 340b to produce hydrogen gas as the reference gas.

Figure 7:
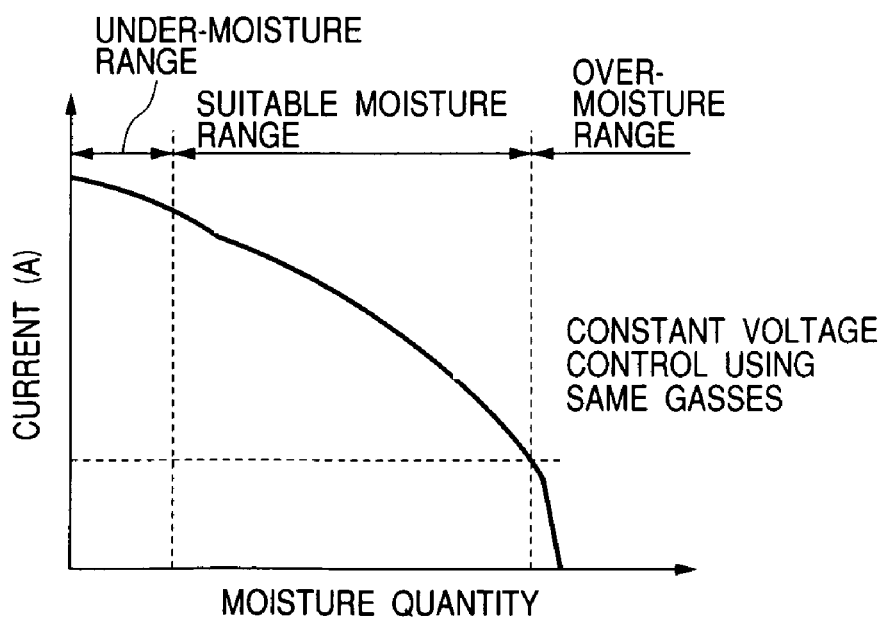
FIG. 7 is a graph which illustrates a relation between a moisture content of a measurement gas and an output current of an electrochemical cell of a moisture quantity sensor when it is placed under constant voltage control in a case where the measurement gas and reference gas are identical in kind with each other.

FIG. 7 illustrates a relation between a moisture content of the measurement gas and an output current of the electrochemical cells 240 and 340 of the moisture quantity sensors 23 and 34 when they are placed under the constant voltage control in a case where the measurement gas and the reference gas are identical in kind with each other.

Keeping a potential difference between the electrodes of each of the moisture quantity sensors 24 and 34 constant under the constant voltage control requires keeping a difference in gas concentration between the electrodes constant. When the moisture content of the measurement gas is increased, it will result in a decrease in concentration of oxygen or hydrogen of the measurement gas, thus causing the quantity of oxygen or hydrogen of the measurement gas consumed in adjusting the concentration of oxygen or hydrogen on the electrode to a desired value to decrease. Specifically, an increase in quantity of moisture contained in the measurement gas results in a decrease in quantity of oxygen or hydrogen of the measurement gas, thus resulting in a decrease in output current of the sensors 24 and 34. Accordingly, a determination of the quantity of moisture within the fuel cell stack 10 may be made by placing the sensors 24 and 34 under the constant voltage control and measuring a resulting value of current produced therefrom. In practice, when the current outputted from the sensors 24 and 34 decreases below a first preselected value, the controller 40 determines that the quantity of moisture in the fuel cell stack 10 has increased over an allowable or suitable range. When the current output exceeds a second preselected value higher in level than the first preselected value, the controller 40 determines that the fuel cell stack 10 lacks in moisture content.

Figure 8:
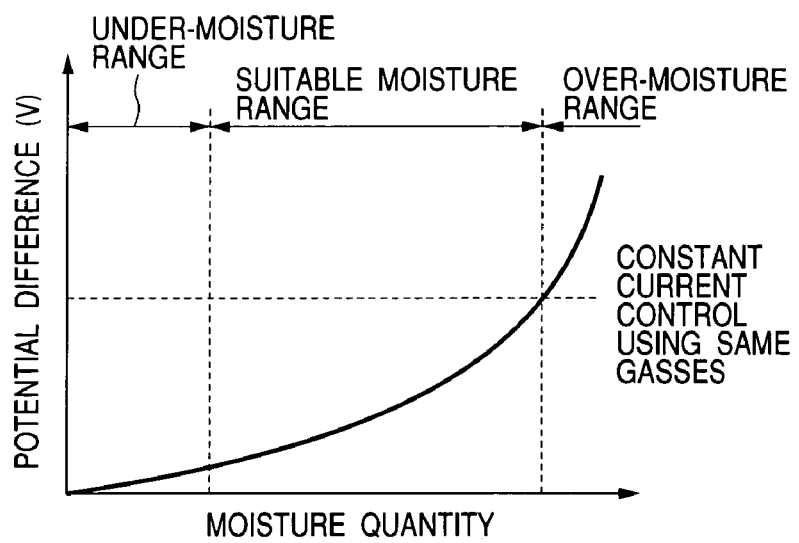
FIG. 8 is a graph which illustrates a relation between a moisture content of a measurement gas and an output voltage of an electrochemical cell of a moisture quantity sensor when it is placed under constant current control in a case where the measurement gas and reference gas are identical in kind with each other.

FIG. 8 illustrates a relation between a moisture content of the measurement gas and an output voltage of the electrochemical cells 240 and 340 of the moisture quantity sensors 23 and 34 when they are placed under the constant current control in a case where the measurement gas and the reference gas are identical in kind with each other.

Usually, the quantity of hydrogen or oxygen gas consumed on the electrodes of the moisture quantity sensors 24 and 34 is constant when the current flowing through the moisture quantity sensors 24 and 34 is kept constant, but however, the concentration of hydrogen or oxygen on the measurement gas electrodes 240a and 340a decreases with an increase in moisture content of the measurement gas, thereby resulting in a change in potential difference between the measurement and reference gas electrodes. Specifically, when the moisture content of the measurement gas increases, it will result in a relative decrease in hydrogen or oxygen concentration of the measurement gas, which causes the potential difference between the measurement and reference gas electrodes to be increased. Therefore, a determination of the quantity of moisture within the fuel cell stack 10 may be made by placing the electrochemical cells 240 and 340 of the moisture quantity sensors 24 and 34 under the constant current control and measuring the potential difference developed between the measurement and reference gas electrodes. In practice, when the potential difference increases above a first preselected value, the controller 40 determines that the quantity of moisture in the fuel cell stack 10 has increased over an allowable range. When the potential difference drops below a second preselected value lower in level than the first preselected value, the controller 40 determines that the fuel cell stack 10 lacks in moisture content thereof.

When the circuit of each of the moisture quantity sensors 24 and 34 is opened, the moisture quantity sensors 24 and 34 exhibit the same characteristics as those in FIG. 8. In this case, the moisture content of the fuel cell stack 10 may be determined by measuring the potential difference between the electrodes of each of the moisture quantity sensors 24 and 34 without controlling the current flowing therethrough.

The fuel cell system of the fourth embodiment will be described below with reference to FIGS. 9 to 11 which is different from the first embodiment in that a moisture quantity sensor is installed within the fuel cell stack 10 instead of the moisture quantity sensors 24 and 34. Other arrangements are identical, and explanation thereof in detail will be omitted here.

Figure 9:
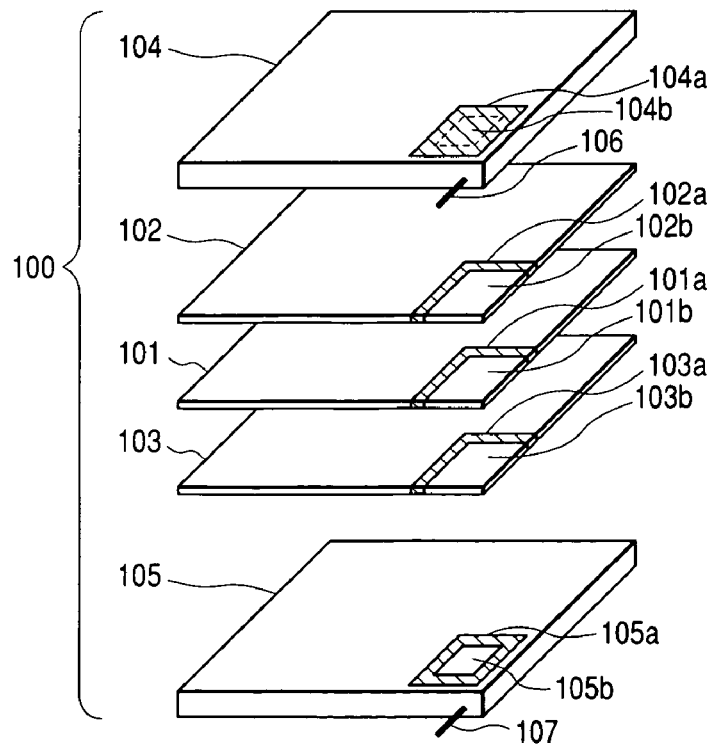
FIG. 9 is an exploded view which shows a modification of a moisture quantity sensor.

FIG. 9 is an exploded view which shows one of the cells 110 of the fuel cell stack 10. The cell 100 is made of a laminate of an electrolyte film 101, a pair of collection plates 102 and 103, and a pair of separators 104 and 105. The collection plates 102 and 103 may be made of carbon cloth. Leads 106 and 107 are connected to the separators 104 and 105, respectively.

The electrolyte film 101, the collection plates 102 and 103, and the separators 104 and 105 have insulating layers 101a, 102a, 103a, 104a, and 105a formed in opposed portions thereof in order to isolate portions 101b, 102b, 103b, 104b, and 105b of the electrolyte film 101, the collection plates 102 and 103, and the separators 104 and 105 electrically from remaining portions thereof. The separators 104 and 105 each have gas supply grooves, not shown, formed in surfaces thereof. The insulating layers 104a and 105a formed in the separators 104 and 105 also work to isolate the portions 101b to 105b from a metal housing, not shown, used to retain the separators 104 and 105.

Figure 10:
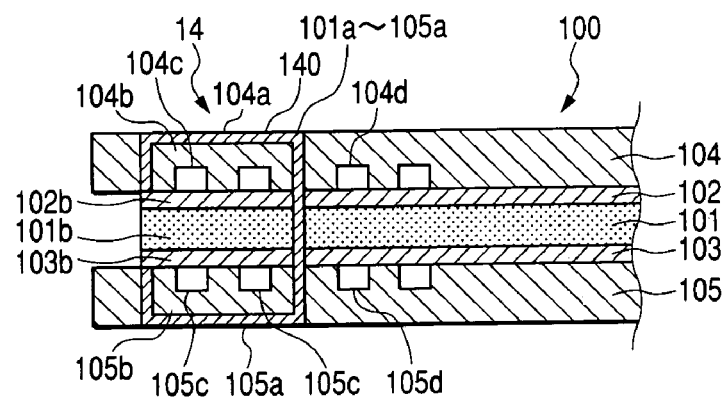
FIG. 10 is a partially sectional view which shows the moisture quantity sensor of FIG. 9.

FIG. 10 is a partially sectional view which shows the cell 100. FIG. 11 is a circuit diagram of the moisture quantity sensor 14 provided within the cell 100 of the fuel cell stack 10. The portions 101b, 102b, 103b, 104b, and 105b of the electrolyte film 101, the collection plates 102 and 103, and the separators 104 and 105 constitute an electrochemical cell 140 of the moisture quantity sensor 14. Of these, the portions 102b, 103b, 104b, and 105b of the collection plates 102 and 103 and the separators 104 and 105 form electrodes of the moisture quantity sensor 14.

The separators 104 and 105 have, as clearly shown in FIG. 10, gas supplying grooves 104c, 104d, 105c, and 105d formed therein. The measurement and reference gasses flow through the gas supplying grooves 104c and 105c of the separators 104 and 105, respectively. As the measurement gas, either of air and hydrogen gas (i.e., gas for power generating) is used. As the reference gas, a gas containing a know quantity of moisture is used which may be identical with or different in kind from the measurement gas. Through the gas supplying grooves 104 and 105, the power generating gasses (i.e., the air and hydrogen gas) flow.

Figure 11:
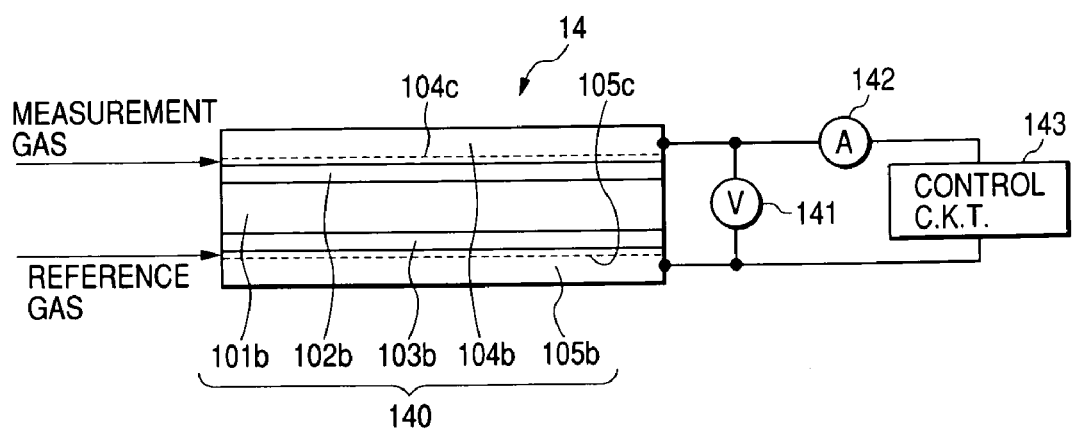
FIG. 11 is a circuit diagram of the moisture quantity sensor of FIG. 9.

The electrochemical cell 140 of the moisture quantity sensor 14 is, as clearly shown in FIG. 11, connected to a control circuit 143 through current and voltage detectors 142 and 141. The control circuit 143 works to place the electrochemical cell 140 under the constant voltage or current control and measures a moisture content of the power generating gasses within the fuel cell stack 10. The moisture quantity sensor 14 may be formed only in any one of the cells 100 of the fuel cell stack 10 which is easy to dry.

The fuel cell system of the fifth embodiment will be described below with reference to FIG. 12 which is different from the fourth embodiment in that the electrochemical cell 140 of the moisture quantity sensor 14 formed independently from the cell 100 is installed in the cell 100. Other arrangements are identical, and explanation thereof in detail will be omitted here.

Figure 12:
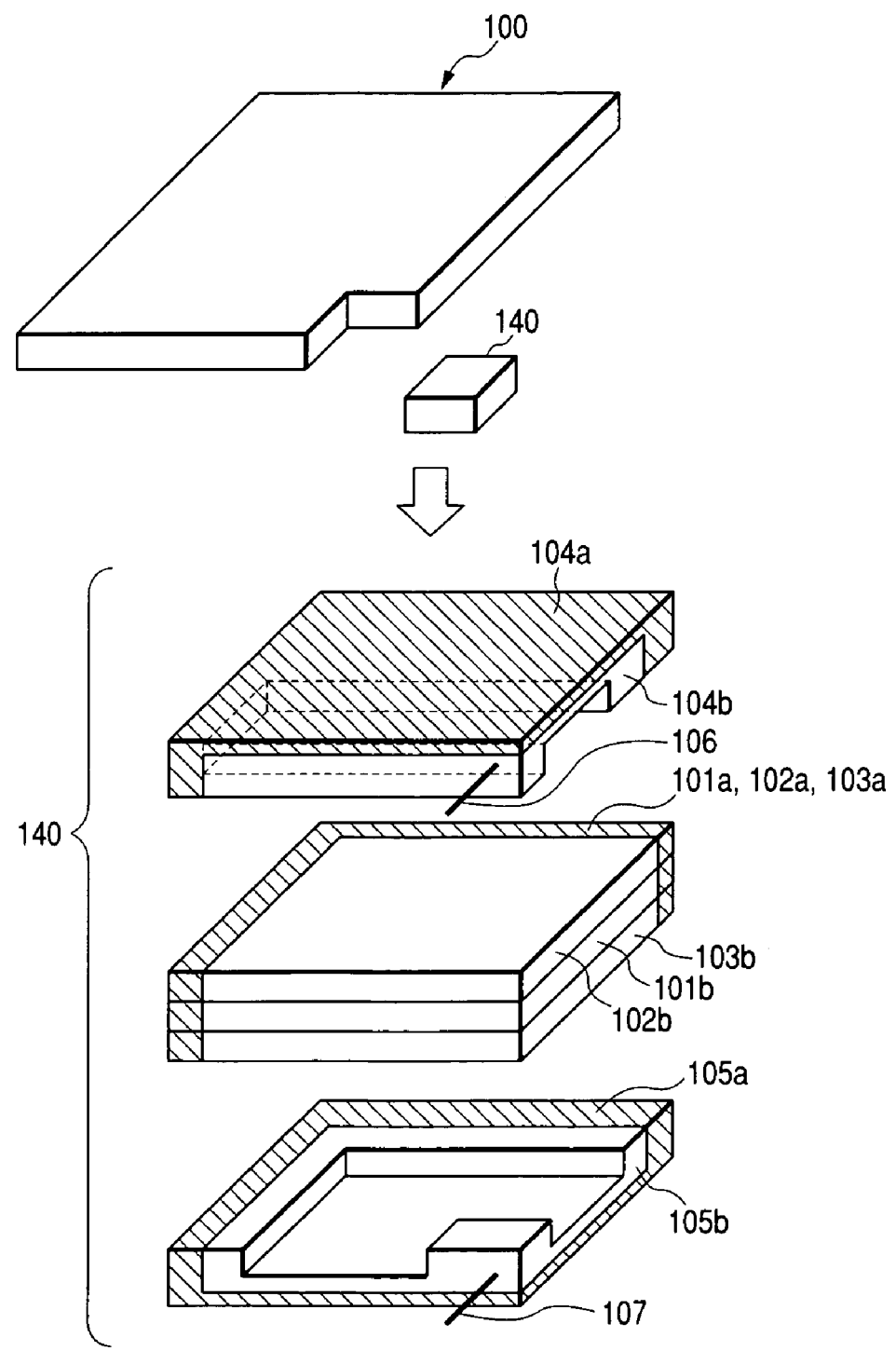
FIG. 12 is a perspective exploded view which shows a second modification of a moisture quantity sensor.
Figure 13:
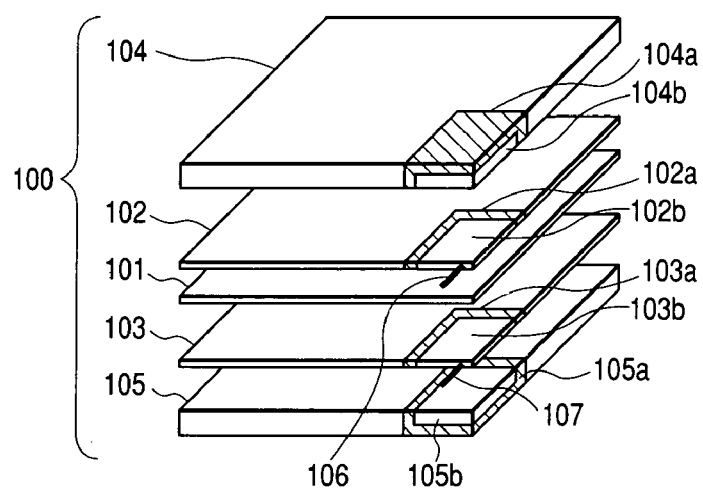
FIG. 13 is a perspective exploded view which shows a third modification of a moisture quantity sensor.
Figure 14:
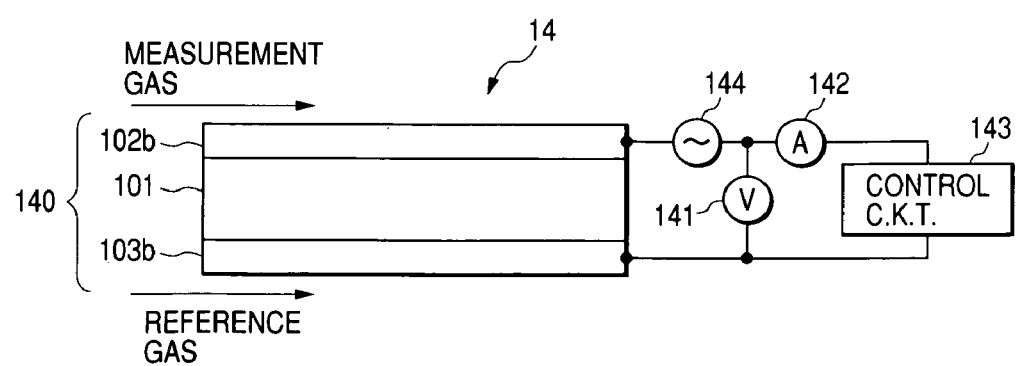
FIG. 14 is a circuit diagram of the moisture quantity sensor of FIG. 13.

The cell 100 has, as clearly shown in FIG. 12, a cutout formed in a corner thereof in which the electrochemical cell 140 is disposed. The electrochemical cell 140 has insulating layers 101a to 105a interposed between a major portion of the electrochemical cell 140 and the cell 100. Outer surfaces of the separators 104b and 105b are covered with the insulating layers 104a and 105a, respectively.

The electrochemical cell 140 of the moisture quantity sensor 14 has a structure similar to that of the cell 100 and is made of a laminate of the collection plates 102b and 103b disposed on opposed sides of the electrolyte film 101b and the separators 104b and 105b. The collection plates 104b and 105b may be made of carbon cloth. The separators 104b and 105b have, as clearly shown in FIG. 12, measurement and reference gas supplying grooves formed therein, respectively. As the measurement gas, either of air and hydrogen gas (i.e., gas for power generating) is used. As the reference gas, a gas containing a know quantity of moisture is used which may be identical with or different in kind from the measurement gas.

The fuel cell system of the sixth embodiment will be described below with reference to FIGS. 13 to 18 which is different from the fourth embodiment in that a moisture content of the cell 100 is measured as a function of a resistance value of the cell 100. The same reference numbers as employed in the fourth embodiment will refer to the same parts, and explanation thereof in detail will be omitted here.

The collection plates 102 and 103 have the insulating layers 102a and 103a formed therein to electrically isolate the portions 102b and 103b from major portions of the collection plates 102 and 103, respectively. The portions 102b and 103b of the collection plates 102 and 103 form electrodes of the electrochemical cell 140. Leads 106 and 107 are joined to the portions 102b and 103b, respectively. The separators 104 and 105 have the insulating layers 104a and 105a formed therein to electrically isolate the portions 104b and 105b from major portions of the separators 104 and 105, respectively.

The moisture quantity sensor 14 is so designed as to measure an internal resistance thereof as a function of an AC impedance. The electrochemical cell 140 is, as clearly shown in FIG. 14, made up of the electrolyte film 101 and the electrodes 102b and 103b which are joined to the control circuit 143. The voltage and current detectors 141 and 142 are installed between the electrochemical cell 140 and the control circuit 143. The sine wave generator 144 is installed between the electrode 102b and the current detector 142 which works to output a sinusoidal current having a selectable frequency.

Figure 15:
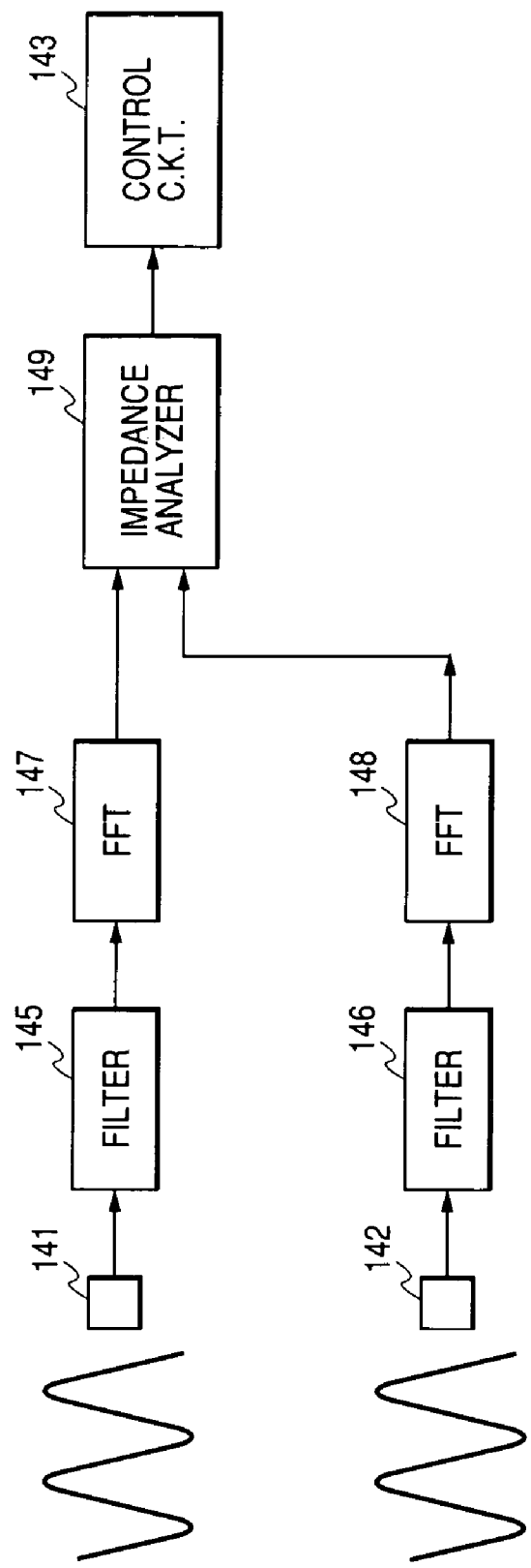
FIG. 15 is a circuit diagram which shows an impedance analyzer used in the circuit of FIG. 14.

The moisture quantity sensor 14 also includes an impedance measuring circuit which consists, as shown in FIG. 15, of filters 145 and 146, FFT (Fast Fourier Transform) processors 147 and 148, and an impedance analyzer 149. The filters 145 and 146 are joined to the voltage detector 141 and the current detector 142, respectively, and work to remove noise components from outputs of the voltage detector 141 and the current detector 142. The FFT processors 147 and 148 work to calculate FFTs of the outputs of the filters 145 and 146 and output them to the impedance analyzer 149. The impedance analyzer 149 works to determine the impedance of the cell 100 using voltage and current components derived through the FFT.

Figure 16:
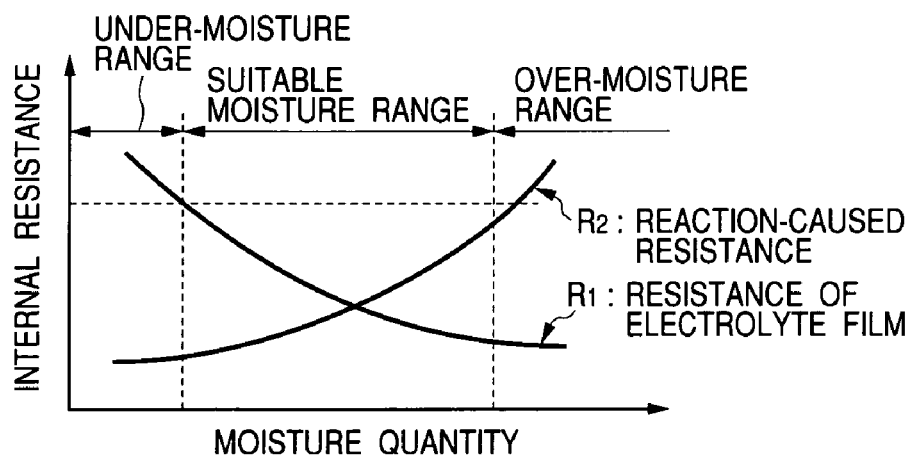
FIG. 16 is a graph which illustrates a relation between a moisture content of a cell of a fuel cell stack and an internal resistance thereof.

FIG. 16 illustrates a relation between a moisture content of the cell 100 of the fuel cell stack 10 and an internal resistance thereof. The graph shows that the moisture content has a correlation to the internal resistance. Specifically, when the quantity of moisture in the cell 100 decreases, it will cause the moisture within the electrolyte film 101 to decrease, thereby resulting in a drop in conductivity of the electrolyte film 101. This results in an increase in resistance of the electrolyte film 101, which will be described later in detail. Accordingly, when the resistance of the electrolyte film 101 exceeds a first preselected value, the controller 40 may determine that the quantity of moisture in the fuel cell stack 10 lacks in moisture content. When the moisture within the cell 100 is excessive, it will result in an increase in reaction-caused resistance of the electrodes of the electrochemical cell 140, which will be described later in detail. Accordingly, when the reaction-caused resistance of the electrodes exceeds a second preselected value, the controller 40 may determine that the moisture in the fuel cell stack 10 is excessive. When another condition is encountered, the controller 40 may determine that the quantity of moisture in the fuel cell stack 10 lies within a suitable range.

A voltage drop of the cell 100 of the fuel cell stack 10 typically results from the reaction-caused resistance produced by the electrochemical reaction and the resistance of the electrolyte film 101 of the cell 100. The reaction-caused resistance and the resistance of the electrolyte film 101 may be measured in the following manner.

Figure 17:
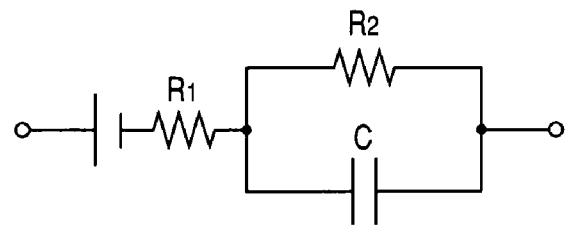
FIG. 17 illustrates an equivalent circuit of a cell of a fuel cell stack.

FIG. 17 illustrates an equivalent circuit of the cell 100 of the fuel cell stack 10. $R_1$ indicates the resistance of the electrolyte film 101. $R_2$ indicates the reaction-caused resistance. Application of a sinusoidal current having a given frequency to the equivalent circuit causes a change in voltage to lag behind a change in the current.

Figure 18:
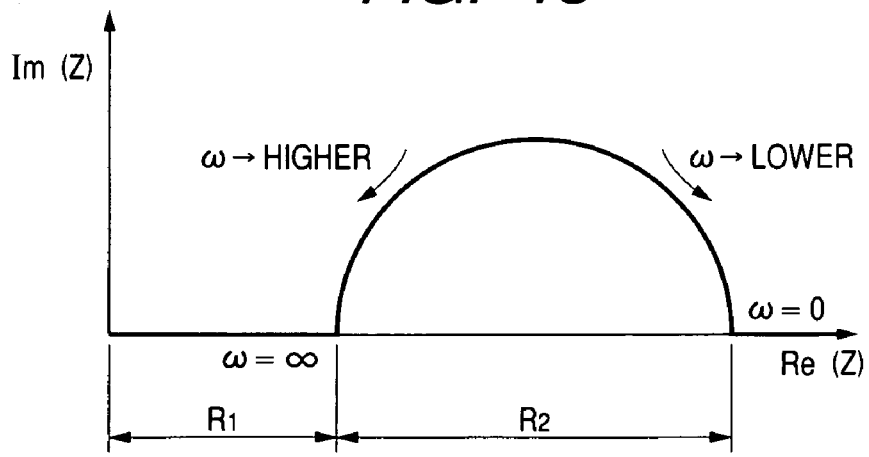
FIG. 18 is a graph which illustrates the impedance of a cell, as expressed on a complex plane, when a sinusoidal current applied to the equivalent circuit of FIG. 17 is changed from high to low frequency wave.

FIG. 18 illustrates the impedance of the cell 100, as expressed on a complex plane, when the sinusoidal current applied to the equivalent circuit is changed from high to low frequency wave. When the frequency of the applied sinusoidal current is infinite ($\omega=\infty$), the impedance is given by $R_1$. Alternatively, when the frequency of the applied sinusoidal current is low ($\omega=0$), the impedance is given by $R_1+R_2$. The impedance when the applied sinusoidal current is changed from high to low frequency wave changes, as clearly shown in the drawing, along a semi-circle.

Specifically, the resistances $R_1$ and $R_2$ may be measured in dependently by changing the frequency of the sinusoidal current applied by the sine wave generator 144 to the electrochemical cell 140. The resistance $R_1$, as described above, indicates the resistance of the electrolyte film 101. Thus, when the resistance $R_1$ exceeds a first preselected value, the controller 40 may determine that the electrolyte film 101 lacks in moisture content. When the resistance $R_1$ is lower than the first preselected value, the controller 40 may determine that the quantity of moisture in the electrolyte film 101 lies within the suitable range. The resistance $R_2$, as described above, indicates the reaction-caused resistance of the electrodes. Thus, when the resistance $R_2$ exceeds a second preselected value, the controller 40 may determine that the moisture on the electrodes is excessive. When the resistance $R_2$ is less than the second preselected value, the controller 40 may determine that the quantity of moisture on the electrodes lies within the suitable range.

The portions 102b and 103b of the collection plates 102 and 103 of the cell 100, as already described, form the electrodes of the electrochemical cell 140 of the moisture quantity sensor 14, so that an output current of the moisture quantity sensor 14 is much smaller than an output current of the cell 100 and hardly impinges upon output of the fuel cell stack 10. This permits the moisture quantity sensor 14 to measure the moisture within the cell 100 during operation of the fuel cell stack 10.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims.

For instance, only one of the moisture quantity sensors 24 and 34 employed in the first embodiment may alternatively be installed in either of the oxygen drain line 21 and the hydrogen drain line 31.

Figure 19:
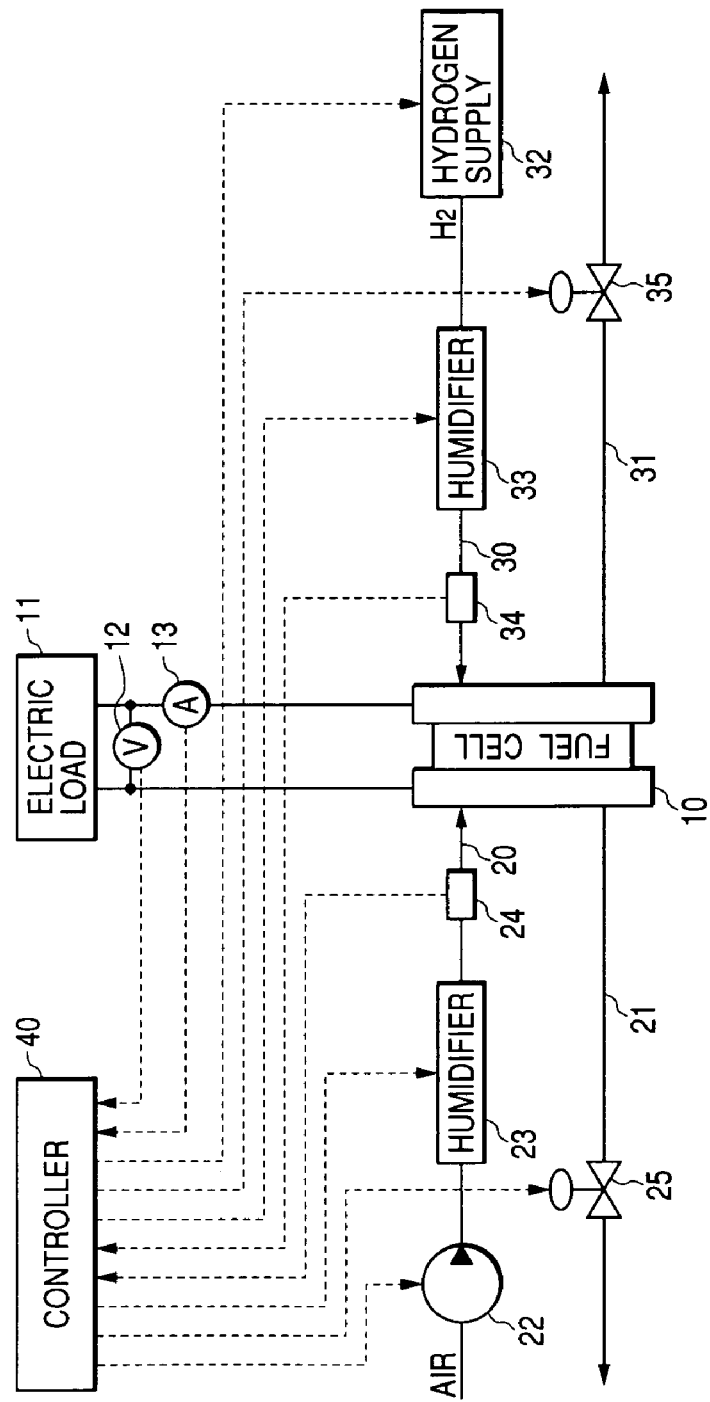
FIG. 19 is a block diagram which shows a modification of a fuel cell system.

The moisture quantity sensors 24 and 34 may be, unlike the first embodiment, installed in the oxygen supply line 20 and the hydrogen supply line 30, as shown in FIG. 19. Alternatively, only one of the moisture quantity sensors 24 and 34 may be installed in either of the oxygen supply line 20 and the hydrogen supply line 30 to measure a moisture content of the air or hydrogen gas supplied to the fuel cell stack 10. The same sensors as the moisture quantity sensors 24 and 34 may be installed both upstream and downstream of the fuel cell stack 10.

The sine wave generator 144 employed in the fuel cell system of the sixth embodiment may alternatively be designed to produce and apply a sinusoidal voltage to a DC voltage outputted by the electrochemical cell 140 of the moisture quantity sensor 14.

The internal resistance of the electrochemical cell 100 is determined by the AC impedance in the sixth embodiment, but may alternatively be determined by increasing an output current of the electrochemical cell 100 gradually and measuring a resulting output voltage thereof to determine a voltage drop.

Figure 20:
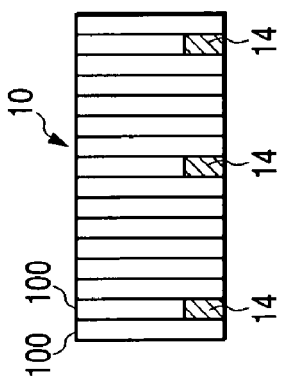
FIG. 20 is a sectional view of a fuel cell stack in which a plurality of moisture quantity sensors are installed.

The same sensors as the moisture quantity sensor 14 constructed by the part of the cell 100 of the fuel cell stack 10 in the fourth to sixth embodiments may be installed, as clearly shown in FIG. 20, in some of the cells 100 of the fuel cell stack 10, thereby enabling a variation in quantity of moisture within the fuel cell stack 10.

What is claimed is:

1. A fuel cell system, comprising:
   a moisture sensor working to measure a moisture content of a measurement gas, said moisture sensor including (a) an electrochemical cell having a first electrode exposed to the measurement gas and a second electrode exposed to a reference gas, said electrochemical cell outputting an electrical energy arising from chemical reaction of the measurement gas with the reference gas, (b) a voltage detector working to measure a voltage appearing at said electrochemical cell, (c) a current detector working to measure a current produced by said electrochemical cell, and (d) a controller controlling at least one of the voltage and the current of said electrochemical cell, said controller determining the moisture content of the measurement gas using one of the voltage and the current and providing a signal indicative thereof;
   a fuel cell producing an electrical energy through chemical reaction between hydrogen and oxygen;
   a moisture controlling mechanism working to control a quantity of moisture within said fuel cell; and
   a system controller working to determine a moisture condition within said fuel cell using the signal outputted from said moisture sensor, said system controller actuating said moisture controlling mechanism to control the quantity of moisture within said fuel cell to a desired value based on the determined moisture condition, wherein the measurement gas and the reference gas are identical in kind with each other, and wherein said controller works to bring a potential difference between the first and second electrodes of said moisture sensor to a given potential difference and determines that the quantity of moisture within said fuel cell is excessive when the current produced by the electrochemical cell is smaller than a first preselected current value.

2. A fuel cell system as set forth in claim 1, wherein said controller determines that said fuel cell lacks in moisture content thereof when the current produced by the electrochemical cell is greater than a second preselected current value.

3. A fuel cell system as set forth in claim 1, wherein said controller determines that the quantity of moisture within said fuel cell is excessive when the a potential difference between the first and second electrodes of the electrochemical cell under control in which said controller controls the current flowing through the electrochemical cell to a given current value is greater than a first preselected potential difference.

4. A fuel cell system as set forth in claim 1, wherein said controller determines that said fuel cell lacks in moisture content when the potential difference between the first and second electrodes of the electrochemical cell under control in which said controller controls the current flowing through the electrochemical cell to a given current value is smaller than a second preselected potential difference.

5. A fuel cell system as set forth in claim 1, further comprising an oxygen gas drain line through which an oxygen gas discharged from an oxygen electrode of said fuel cell flows and a hydrogen gas drain line through which a hydrogen gas discharged from a hydrogen electrode of said fuel cell flows, and wherein said moisture sensor is installed in at least one of said oxygen gas drain line and said hydrogen gas drain line to measure a moisture content of at least one of the hydrogen gas and the oxygen gas discharged from said fuel cell.

6. A fuel cell system as set forth in claim 1, further comprising an oxygen supply line through which an oxygen gas is supplied to said fuel cell and a hydrogen gas supply line through which a hydrogen gas is supplied to said fuel cell, and wherein said moisture sensor is installed in at least one of said oxygen gas supply line and said hydrogen gas supply line to measure a moisture content of at least one of the hydrogen gas and the oxygen gas supplied to said fuel cell.

7. A fuel cell system as set forth in claim 1, wherein said moisture sensor is installed within said fuel cell and works to measure a moisture content of at least one of an oxygen or a hydrogen gas within said fuel cell.

8. A fuel cell system as set forth in claim 7, wherein the electrochemical cell of said moisture sensor is formed by a portion of said fuel cell.

9. A fuel cell system as set forth in claim 7, further comprising moisture sensors installed in some of the cells of said fuel cell stack which are identical in structure with said moisture sensor.

10. A fuel cell system, comprising:
a moisture sensor working to measure a moisture content of a measurement gas, said moisture sensor including (a) an electrochemical cell having a first electrode exposed to the measurement gas and a second electrode exposed to a reference gas, said electrochemical cell outputting an electrical energy arising from chemical reaction of the measurement gas with the reference gas, (b) a voltage detector working to measure a voltage appearing at said electrochemical cell, (c) a current detector working to measure a current produced by said electrochemical cell, and (d) a controller controlling at least one of the voltage and the current of said electrochemical cell, said controller determining the moisture content of the measurement gas using one of the voltage and the current and providing a signal indicative thereof;
a fuel cell producing an electrical energy through chemical reaction between hydrogen and oxygen;
a moisture controlling mechanism working to control a quantity of moisture within said fuel cell; and
a system controller working to determine a moisture condition within said fuel cell using the signal outputted from said moisture sensor, said system controller actuating said moisture controlling mechanism to control the quantity of moisture within said fuel cell to a desired value based on the determined moisture condition, wherein the measurement gas and the reference gas are different in kind from each other, and wherein said controller works to bring the voltage of the electrochemical cell to a given voltage and determines that the quantity of moisture within said fuel cell is excessive when the current produced by the electrochemical cell is smaller than a first preselected current value.

11. A fuel cell system as set forth in claim 10, wherein said controller determines that said fuel cell lacks in moisture content thereof when the current produced by the electrochemical cell is greater than a second preselected current value.

12. A fuel cell system, comprising:
a moisture sensor working to measure a moisture content of a measurement gas, said moisture sensor including (a) an electrochemical cell having a first electrode exposed to the measurement gas and a second electrode exposed to a reference gas, said electrochemical cell outputting an electrical energy arising from chemical reaction of the measurement gas with the reference gas, (b) a voltage detector working to measure a voltage appearing at said electrochemical cell, (c) a current detector working to measure a current produced by said electrochemical cell, and (d) a controller controlling at least one of the voltage and the current of said electrochemical cell, said controller determining the moisture content of the measurement gas using one of the voltage and the current and providing a signal indicative thereof;
a fuel cell producing an electrical energy through chemical reaction between hydrogen and oxygen;
a moisture controlling mechanism working to control a quantity of moisture within said fuel cell; and
a system controller working to determine a moisture condition within said fuel cell using the signal outputted from said moisture sensor, said system controller actuating said moisture controlling mechanism to control the quantity of moisture within said fuel cell to a desired value based on the determined moisture condition, wherein the measurement gas and the reference gas are different in kind from each other, and wherein said controller determines that the quantity of moisture within said fuel cell is excessive when a value of the voltage of the electrochemical cell under control in which the current flowing through the electrochemical cell is kept at a given current value is smaller than a first preselected voltage value.

13. A fuel cell system, comprising:
a moisture sensor working to measure a moisture content of a measurement gas, said moisture sensor including (a) an electrochemical cell having a first electrode exposed to the measurement gas and a second electrode exposed to a reference gas, said electrochemical cell outputting an electrical energy arising from chemical reaction of the measurement gas with the reference gas, (b) a voltage detector working to measure a voltage appearing at said electrochemical cell, (c) a current detector working to measure a current produced by said electrochemical cell, and (d) a controller controlling at least one of the voltage and the current of said electrochemical cell, said controller determining the moisture content of the measurement gas using one of the voltage and the current and providing a signal indicative thereof;
a fuel cell producing an electrical energy through chemical reaction between hydrogen and oxygen;
a moisture controlling mechanism working to control a quantity of moisture within said fuel cell; and
a system controller working to determine a moisture condition within said fuel cell using the signal outputted from said moisture sensor, said system controller actuating said moisture controlling mechanism to control the quantity of moisture within said fuel cell to a desired value based on the determined moisture condition, wherein the measurement gas and the reference gas are different in kind from each other, and wherein said controller determines said fuel cell lacks in moisture content thereof when a value of the voltage of the electrochemical cell under control in which the current flowing through the electrochemical cell is kept at a given current value is greater than a second preselected voltage value.

14. A fuel cell system comprising:
a fuel cell stack including a plurality of cells each of which is made up of a pair of collection members and an electrolyte film disposed between the collection members;
a moisture sensor working to measure a quantity of moisture within at least one of the cells and output a signal indicative thereof;
a moisture controlling mechanism working to control a moisture content of said fuel cell stack; and
a system controller working to determine a moisture condition within said fuel cell stack using the signal outputted from said moisture sensor, said system controller actuating said moisture controlling mechanism to control the quantity of moisture within said fuel cell stack to a desired value based on the determined moisture condition,
wherein said moisture sensor includes (a) an electrochemical cell having electrodes formed by portions of the pair of collection members of the cell and said electrolyte film and (b) a resistance measuring circuit working to measure a resistance value of said electrochemical cell, and wherein the quantity of moisture within the cell is determined as a function of the resistance value of said electrochemical cell.

15. A fuel cell system as set forth in claim 14, wherein said resistance measuring circuit is designed to apply a sinusoidal wave signal to an output signal of said electrochemical cell and change a frequency of the sinusoidal wave signal to measure an AC impedance of said electrochemical cell, said resistance measuring circuit determines a resistance value of said electrolyte film and a reaction-caused resistance value of the electrodes of said electrochemical cell.

16. A fuel cell system as set forth in claim 15, wherein said system controller determines that said fuel cell stack lacks in moisture content thereof when the resistance value of the electrolyte film is greater than a first preselected resistance value.

17. A fuel cell system as set forth in claim 16, wherein said system controller determines that the quantity of moisture within said fuel cell stack lies within an allowable range when the resistance value of the electrolyte film is smaller than the first preselected resistance value and when the reaction-caused resistance value is smaller than a second preselected resistance value.

18. A fuel cell system as set forth in claim 17, wherein said system controller determines that the quantity of moisture within said fuel cell stack is excessive when the reaction-caused resistance value is greater than the second preselected resistance value.

* * * * *